(12) United States Patent
Merkel (10) Patent No.: US 11,982,180 B2
(45) Date of Patent: May 14, 2024

(54) ARRANGEMENT, DRILL RIG AND METHOD THEREIN FOR DETECTION OF WATER IN MATERIAL FLOW

(71) Applicant: EPIROC ROCK DRILLS AKTIEBOLAG, Örebro (SE)

(72) Inventor: Harald Franz Arno Merkel, Ringkøping (DK)

(73) Assignee: EPIROC ROCK DRILLS AKTIEBOLAG, Örebro (SE)

( * ) Notice: Subject to any disclaimer, the term of this patent is extended or adjusted under 35 U.S.C. 154(b) by 58 days.

(21) Appl. No.: 17/913,231

(22) PCT Filed: Mar. 31, 2021

(86) PCT No.: PCT/SE2021/050292
§ 371 (c)(1),
(2) Date: Sep. 21, 2022

(87) PCT Pub. No.: WO2021/211034
PCT Pub. Date: Oct. 21, 2021

(65) Prior Publication Data
US 2023/0140058 A1 May 4, 2023

(30) Foreign Application Priority Data
Apr. 14, 2020 (SE) .................... 2050420-5

(51) Int. Cl.
G01N 27/02 (2006.01)
E21B 47/00 (2012.01)
(Continued)

(52) U.S. Cl.
CPC ............ *E21B 47/138* (2020.05); *E21B 47/07* (2020.05); *E21B 2200/22* (2020.05)

(58) Field of Classification Search
None
See application file for complete search history.

(56) References Cited

U.S. PATENT DOCUMENTS

| 6,272,915 B1 * | 8/2001 | Kostelnicek ......... E21B 47/047 |
| | | 73/152.55 |
| 6,456,093 B1 | 9/2002 | Merkel et al. |
| | | (Continued) |

FOREIGN PATENT DOCUMENTS

| KR | 20160096339 A | 8/2016 |
| SE | 517315 C2 | 5/2002 |
| | (Continued) | |

OTHER PUBLICATIONS

International Search Report and Written Opinion dated Jul. 13, 2021 for International Application No. PCT/SE2021/050292, 8 pages.
(Continued)

*Primary Examiner* — Curtis A Kuntz
*Assistant Examiner* — Jerold B Murphy
(74) *Attorney, Agent, or Firm* — Sage Patent Group (57) ABSTRACT

Arrangement for detecting water in a material flow during drilling, wherein the arrangement includes a control unit, a data acquisition unit and a sensor, wherein the sensor includes at least two probes, wherein the at least two probes are to be arranged in contact with the material flow and are connected to a programmable voltage source and a programmable voltage receiver. The arrangement is configured to measure a ratio between a received voltage waveform and an applied voltage waveform for a set of pre-determined frequencies; determine a complex impedance between the at least two probes for each of the pre-determined frequencies, based on the measured ratio; and determine a set of time mean values of the determined complex impedance for each of the pre-determined frequencies, using a time window.

16 Claims, 3 Drawing Sheets

(51) Int. Cl.
*E21B 47/07* (2012.01)
*E21B 47/12* (2012.01)
*G01N 27/08* (2006.01)

(56) References Cited

U.S. PATENT DOCUMENTS

| | | |
|---|---|---|
| 7,679,375 B2 | 3/2010 | Merkel |
| 8,076,950 B2 | 12/2011 | Wee |
| 10,001,453 B2 * | 6/2018 | Pagani ................. G01N 27/223 |
| 2003/0024315 A1 | 2/2003 | Merkel et al. |
| 2006/0098211 A1 | 5/2006 | Merkel et al. |
| 2008/0110242 A1 | 5/2008 | Merkel |
| 2009/0088985 A1 * | 4/2009 | Wee ........................... G01F 1/66 |
| | | 702/30 |
| 2011/0304498 A1 | 12/2011 | Yanagihara et al. |
| 2017/0199142 A1 | 7/2017 | Fusamae |
| 2017/0350740 A1 * | 12/2017 | Mohr ................... G01N 27/026 |
| 2020/0124552 A1 * | 4/2020 | Hu ....................... G01N 27/026 |

FOREIGN PATENT DOCUMENTS

| | | |
|---|---|---|
| SE | 517701 C2 | 7/2002 |
| SE | 528552 C2 | 12/2006 |

OTHER PUBLICATIONS

Bolomey et al.; "Microwave Tomography: From Theory to Practical Imaging Systems"; International Journal of Imaging Systems and Technology, vol. 2, Issue 2, Summer 1990; Abstract; 1 page.

* cited by examiner

ARRANGEMENT, DRILL RIG AND METHOD THEREIN FOR DETECTION OF WATER IN MATERIAL FLOW

CROSS-REFERENCE TO RELATED APPLICATIONS

This application is a 35 U.S.C. § 371 national stage application for International Application No. PCT/SE2021/050292, entitled "ARRANGEMENT, DRILL RIG AND METHOD THEREIN FOR DETECTION OF WATER IN MATERIAL FLOW", filed on Mar. 31, 2021, which itself claims priority to Swedish Patent Application No. 2050420-5, filed on Apr. 14, 2020, the disclosures and contents of which are hereby incorporated by reference in their entireties.

FIELD OF THE INVENTION

The invention relates to the field of mining industry, e.g. rock breaking or rock drilling. In particular the invention relates to detecting water in material flow while drilling.

BACKGROUND OF THE INVENTION

Rock drilling or rock breaking is today widely used in many industries, such as oil, gas, well drilling, mining, infrastructure construction and civil engineering. There are a number of different drilling techniques used, e.g. rotary-percussive drilling and rotary drilling. The choice of drilling technique depends on the specific application where the type of rock formation, depth and diameter of the drilling hole are of importance.

During drilling in, e.g. a rock, a material flow is created. The material flow may comprise cut stone particles but also dust and/or sand. A filter may be used to separate the cut stone particles, dust and/or sand from the air. Under the presence of water in the material flow, the particles and water may form a solidifying layer on the filter requiring the filter to be frequently changed. It is therefore useful to detect water in the material flow during drilling. With the goal of tele commanding drill units, automated water detection is a requirement.

U.S. Pat. No. 8,076,950 B2 discloses a method for determining water conductivity and water volume fraction of a multi-component mixture of water and at least one additional liquid or gas in a pipe. The method is based on a measurement of a complex dielectric constant of the multi-component mixture, which complex dielectric constant is determined by measuring a wave phase constant of a plane electromagnetic wave propagating near the inside wall of the pipe. The measurement of the wave phase constant is based on a measurement of a phase difference between two receiving antennas inside the pipe located at different distances from a third transmitting antenna. The phase measurement is performed in at least two frequencies in the range between 10 MHz and 10 GHz. The method presents high to medium water contents, wherein the water contamination in material flows is far too low to influence the phase speed in the medium in a detectable way. Even worse, water being bound to solid particles will not exhibit the usual dielectric behavior, described by values of the relative dielectric function of around 60-80. Bound water will not exhibit a relative dielectric function larger than 2-5. Phase measurements on the bulk dielectric behavior are not very sensitive.

U.S. Pat. No. 7,679,375 B2 discloses a method for detection of foreign objects in a product. The method responds to rapid changes in the dielectric composition of the material flow. Measurement takes place in transmission and the measurement results are not used to calculate a dielectric function of the material but are depicted in a Poincare curve. This is to include scatter signals of small objects. The aim of the method is to detect objects smaller than the wavelength of the radar signal used and to detect objects with lower dielectric function than the surroundings.

WO 2006052202 A1 relates to a method for determining physical parameters, such as temperature or density, inside an object by determining the dielectric function of the object. For the method, coherent and simultaneous application of ultrasound and microwave signals requires alternative application of microwave signals with such effect that non-linear material properties begin to be visible. Thus, requires ultrasound induced change of density in a material. Such an ultrasound induced change in density requires a non-elastic medium. Therefore this method is not applicable in a system that contains air.

WO 0218920 A1 discloses a method and a device for measuring the distribution of selected properties in a material, and in particular a device that non-contacting and non-destructively measures the spatial distribution of material properties, such as density, water contents and temperature of materials, by detecting electromagnetic radiation.

None of the above methods present a viable solution to measure water contents low enough as required to prevent filter blocking. The water contents dealt with is so low that a volumetric measurement of any property change is not possible. In addition, natural changes of the volumetric properties of the material flow, such as changes in the stone character or density, will be much more pronounced than the presence of water. There is thus a need for improvement in this technical field.

BRIEF DESCRIPTION OF EMBODIMENTS HEREIN

It is an object of embodiments herein to enhance water detection performance in material flow during drilling, or at least to achieve an alternative to known solutions within the technical field.

According to an aspect the object is achieved by providing an arrangement adapted for detecting water in a material flow during drilling. The arrangement comprises a control unit, a data acquisition unit and a sensor. The sensor comprises at least two probes. The at least two probes are to be arranged in contact with the material flow and are connected to a programmable voltage source and a programmable voltage receiver. The arrangement is configured to measure a ratio between a received voltage and an applied voltage for a set of pre-determined frequencies. The arrangement is further configured to determine a set of complex impedance between the at least two probes for each of the pre-determined set of frequencies, based on the measured ratio. The arrangement is further configured to determine a set of time mean values of the determined complex impedance for each of the pre-determined frequencies, using a time window. The arrangement is further configured to determine a set of standard deviations, based on the determined time mean values. The arrangement is further configured to indicate that water is detected when at least one of said standard deviations exceeds a threshold condition.

According to another aspect the above mentioned object is also achieved by providing a method for detecting water in a material flow during drilling. The method comprises measuring a ratio between a received voltage waveform and an applied voltage waveform for a set of pre-determined frequencies. The method further comprises determining a set of complex impedance between at least two probes for each of the pre-determined set of frequencies, based on the measured ratio. The method further comprises determining a set of time mean values of the determined complex impedance, using a time window. The method further comprises determining a set of standard deviations, based on the determined time mean value. The method furthermore comprises indicating that water is detected when at least one of said standard deviations exceeds a threshold condition.

It is furthermore provided herein a drill rig comprising an arrangement for detecting water in a material flow.

By arranging the at least two probes in contact with the material flow during drilling and measuring the ratio between the received voltage and the applied voltage, the complex impedance for each of the pre-determined frequencies between the probes can be determined as it is based on measured ratio. And by determining a set of time mean values of the determined complex impedance and determining a set of standard deviations, based on the determined time mean values, it can be indicated that water is detected when at least one of said standard deviations exceeds a threshold condition. Thereby the water detection performance in material flow during drilling is enhanced and more optimized. A more optimized and enhanced water detection performance will lead to a decreased wear and tear of the filter and the filter will not need to be as frequently changed.

Consequently, a method and an arrangement for detecting water in a material flow during drilling is achieved.

BRIEF DESCRIPTION OF THE FIGURES

Further objects and advantages, as well as technical features of the invention will become apparent through the following description of one or several embodiments given with reference to the appended figures, where.

It should be noted that the drawings has not necessarily been drawn to scale and that the dimensions of certain elements may have been exaggerated for the sake of clarity.

DETAILED DESCRIPTION OF EMBODIMENTS HEREIN

The present invention is described in more detail below with reference to the appended figures, in which examples of embodiments are shown. The invention is not limited to the described examples of embodiments; it is rather defined by the appended patent claims. Like numbers in the figures refer throughout to like elements.

Figure 1:
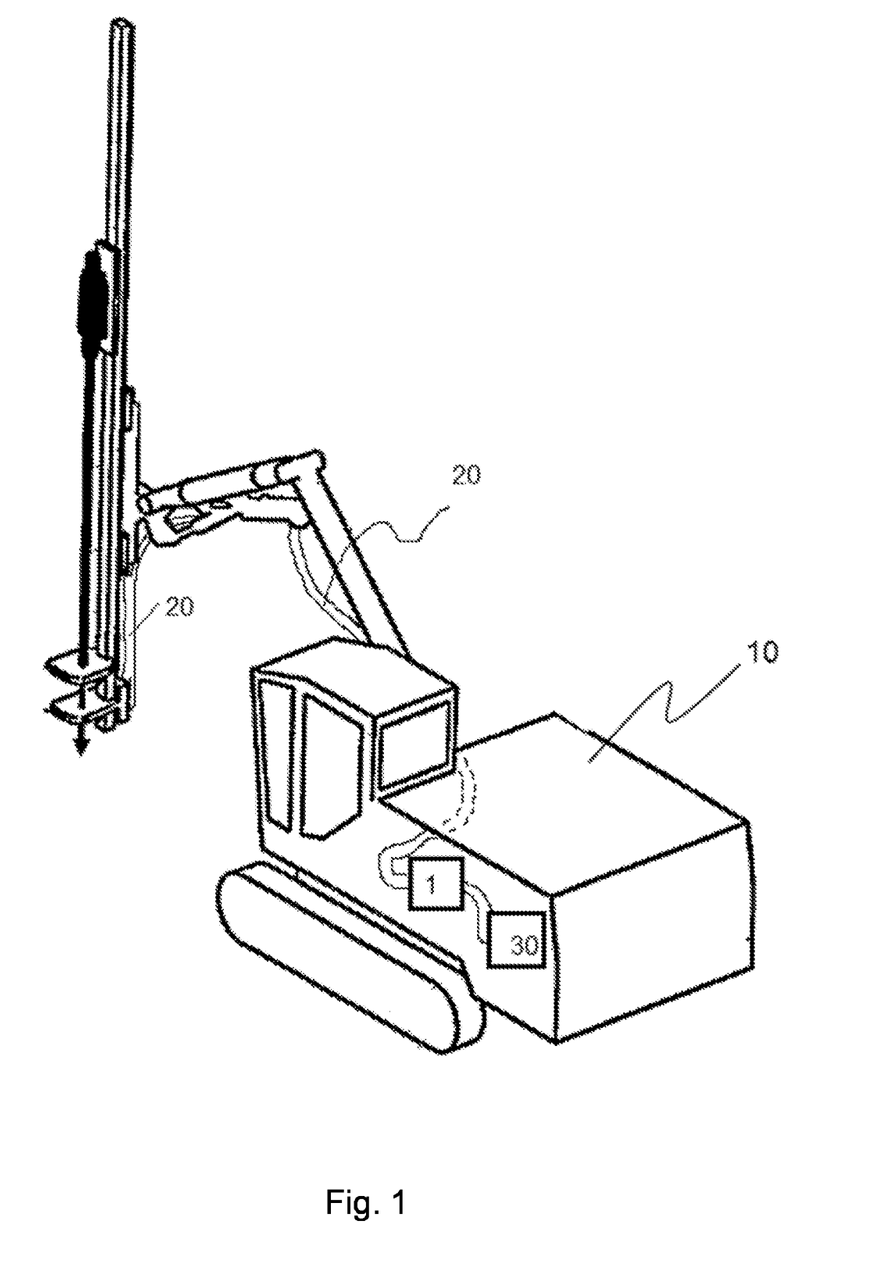
FIG. 1 is a schematic overview of an exemplifying arrangement, placed on a drill rig, for detecting water in a material flow during drilling.

FIG. 1 illustrates a schematic overview of embodiments herein comprising an arrangement 1 adapted for detecting water in a material flow during drilling, e.g. rock drilling. The arrangement 1 is placed on a drill rig 10 in the material flow 20 in front of a filter 30, e.g. a material filter used to separate the cut stone particles, dust and/or sand from the air.

Figure 2:
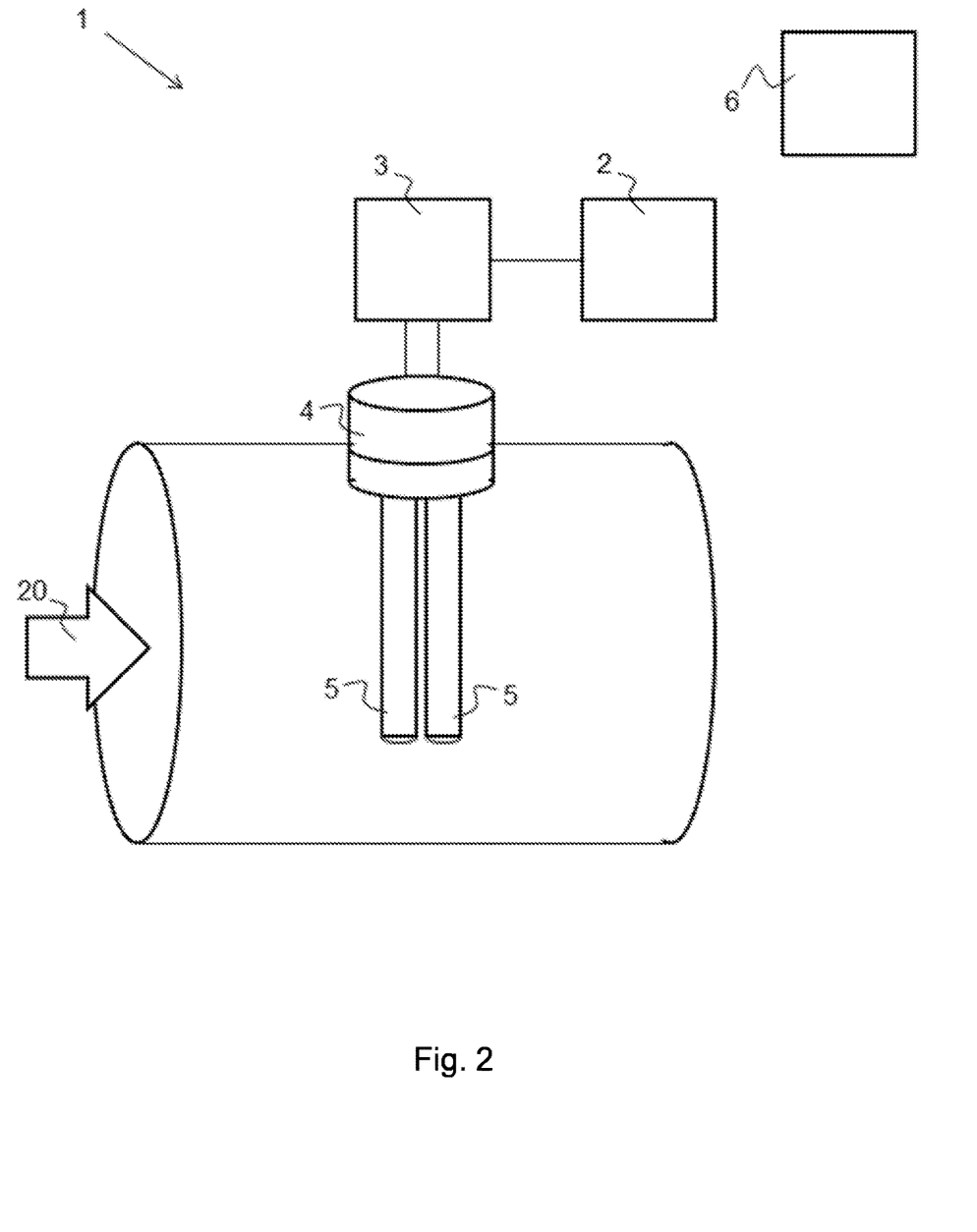
FIG. 2 is a schematic view of an exemplifying arrangement for detecting water in a material flow during drilling.

The arrangement 1 for detecting water in the material flow 20 during drilling is illustrated in FIG. 2. The arrangement 1 comprises a control unit 2, a data acquisition unit 3 and a sensor 4. The arrangement 1 may also comprise a remote unit 6 to repeat the indication of the detection of water to a drill rig operator.

The material flow 20, which may also be referred to as drill cut flow, drill flow or material back flow, is the return drill flow and may e.g. comprise a gaseous component consisting of predominantly air, a set of solid components comprising sand, dust and stone particles, a set of liquid components with the presence of water and/or a set of dissolved components in said liquids.

The control unit 2 may e.g. be a controller such as a microcontroller, a microprocessor, a data logger unit or other digital hardware, configured to perform the method herein. The control unit 2 comprises a display to indicate system state and connected buttons for restart or manual water presence detection. The data acquisition unit 3 may e.g. be a compact signal generator.

The data acquisition unit 3 is completely galvanically separated from the probes 5. This is a requirement to avoid damage and destruction to the electronics in dry environment where the material flow 20 will statically charge the sensor heads. Therefore, the arrangement 1 is also suited for dielectric or piezoelectric rock types prone to charging effects and prone to triboelectric effects.

In addition, the used voltage levels may be of the order of 5V, which is far below the generation of sparks or discharges. Consequently, the arrangement 1 is also suitable to be used in environments with explosion risk e.g. in natural gas sources or coal mines.

The sensor 4, e.g. a probe holder, comprises a plurality of probes 5 which may be arranged in pairs. The probes 5 are to be arranged in contact with the material flow 20 and are connected to a programmable voltage source and a programmable voltage receiver.

The probes 5, e.g. pairs of probes 5, may be designed to provide an as small as possible capacitance gap and an as long as possible resistance measurement line in between them and within the material flow 20. According to some embodiments the probes 5 may be made of metal. All embodiments have in common that the probes 5 may be at least partly conductive. The choice of metal may be made in order to achieve a long life time of the probes 5 in the material flow 20.

A large resistively sensitive line yields large absolute changes in conductivity in the imaginary part of the complex impedance. A small capacitive gap along a long line yields a large measurable capacitance. Therefore the absolute changes of capacitance are large as well. This property is especially well implemented by curve forms such as meander structures, Sierpinski or Peano curves.

The arrangement 1 is configured to measure a ratio between a received voltage waveform and an applied voltage waveform for a set of pre-determined frequencies and to determine a set of complex impedances between the at least two probes 5 for each of the pre-determined frequencies, based on the measured ratio. The set of complex impedance values are considered as coordinates in a higher dimensional Euclidian vector space. E.g. N predetermined frequencies lead to N complex coordinates consisting of 2N coordinate values. Thus, the measurement is described by a point in a 2N-dimensional vector space. Since this space is treated as a Euclidean space, concept as distance, mean values remain valid. The arrangement 1 is further configured to determine a set of time mean values of the determined complex impedance for each of the pre-determined frequencies, using a time window, and to determine a set of standard deviations, based on the determined time mean values. The arrangement 1 is further configured to indicate that water is detected when at least one of said standard deviations exceeds a threshold condition. I.e., configured to comprise an indicator criterion, which if the local measured point's distance to the mean value exceeds a predetermined geometrical form, will act as a threshold condition.

According to some embodiments, each of the at least two probes 5 may comprise one or more heaters. There may be one heater per pair of probes 5. The heaters may be adapted to be controlled externally, e.g. in an on-off way, in order to stabilize the temperature to predetermined values. The heaters may be resistive. Typical resistive heaters may be commercially available heater elements for 24V soldering irons. Heating powers of 200 W-500 W may generally be sufficient. The heater serves two distinct purposes:

The heater may be switched on as soon as the sensor 4 detects water. As soon as water is detected by a substantial change of the properties found in the measured set of impedances, this change persists until the water has either dried off or has been otherwise removed by the flow 20. During this time, no useful measurement is possible. This time is referred to as blind time. This time is typically of the range of seconds which does not interfere substantially with the operation of the drill. Nevertheless, one may want to reduce the blind time or enforce a restart on dry conditions. This is done by activating the heater until the probe dries off.

The heater may also be switched on regularly to detect the presence of water in conductive material flow 20 by using an indirect heat capacitance measurement. Under the presence of water, the measured set of impedance will correlate with the heater activity. If no water is present, no correlation between the set of impedance and the heater state is found. Therefore this method is self-calibrating with respect to changes in the drilled stone's properties.

According to some embodiments, one of the at least two probes 5 may comprise one or more heaters, wherein the heaters may be adapted to be controlled externally in order to stabilize the temperature to a set of predetermined values. One of the at least two probes 5, which may be referred to as an ambient probe, is left at ambient temperature, which may be assumed to be less than 100 C, and one of the at least two probes 5, which may be referred to as a heated probe, is heated to a temperature slightly larger than 100 C. Due to convective cooling, the temperature of the heated probe, is lowered by the material flow 20 and may need to be constantly stabilized. The complex impedance may be measured in both of the probes 5. The ambient probe may yield a potentially water-contaminated signature. The probe being at a temperature larger than 100 C will yield a dry signature under all circumstances. The ambient probe will yield a signature that is eventually contaminated with water. As long as the material flow 20 does not contain any water, both responses are equal, within the reproducibility of the measurement. As soon as the material flow 20 will contain water, there will be a difference. Recording this difference of the set of the complex impedances detects the presence of water in the first way. In the first way may mean directly, with no time integration or mean value required.

However, on the impact of especially larger quantities of water, the real parts of the sets of complex impedances may drop substantially on both the heated probe and the ambient probe. Both probes will thus exhibit a blind time. Nevertheless, the blind time on the heated probe will be considerably smaller compared to the blind time on the ambient probe. This difference in return slope can be used as a way to detect the presence of water in a second way.

Using this second way, it is possible to apply a heater to the ambient probe as well in order to reduce the blind time of the sensor. Special care should be taken in this case as this additional heater may create a situation where both probes 5 are hot and water will remain undetected. Since the α-error, i.e. not detecting water when there is water, should be avoided it has been proven more effective to accept a higher β-error instead, i.e. detecting water where there is none. These indirect heat capacitance measurements enable self-calibrating on short time delays. Another advantage is that the temperature of the heated probe may e.g. be set to 125 C instead of 360 C in the on-off case.

According to some embodiments, each of the at least two probes 5 may comprise one or more heaters, wherein the heaters are adapted to be controlled externally in order to monitor heating current and/or temperature. I.e. the ability to monitor the current through the heaters and/or the temperature of the heater has been added. The presence of water may be indicated by a dip in the real parts of the sets of differences between the heated and non-heated electrode pairs, e.g. pairs of probes 5. At the same time, on the sudden presence of water, there may be a significant increase of the heater current. Water in the material flow 20 may be evaporated which causes more efficient cooling of the heated probe. No such effect is present in the ambient pair of probes. The peak in heating current together with the dip in differential impedance is a clear indication for water under almost all circumstances. These indirect heat capacitance measurements enable low β-error and self-calibrating on short time delays. Another advantage is that the temperature of the heated probe may e.g. be set to 125 C instead of 360 C in the on-off case.

According to some embodiments, the sensor 4 comprises at least three probes 5, wherein each of the three probes 5 comprises one or more heaters. The heaters are adapted to be controlled externally in order to monitor heater current and in order to measure temperature. The probes 5 may be heated to given and distinct temperatures. Using these embodiments it is possible to limit the temperatures to below 100 C. Then the measurement may no longer be based on the evaporation energy required, but simply on the chill effect: Having a material flow 20 that is essentially and in average drier than the accumulated material on the probes 5, the accumulated material on the probes 5 is in evaporation equilibrium with the flow 20. Drying a probe will thus cool the probe and the cooling of the probe is measured by directly measuring the temperature of the probe or by indirectly measuring the required heater energy required to keep the temperature at a predetermined level. Since the relation between required heaters is a function of temperature, three temperature points are sufficient to establish the presence of an evaporation equilibrium.

According to some embodiments, the heaters may be resistive. As described above, it is possible to monitor the current and/or the temperature through the resistive heaters. Now, the presence of water is indicated by a set of dips in the real part of the difference between any of the heated and non-heated pairs of probes 5. At the same time, a significant increase of the heater current in the heated probes may occur. Since the heated probes are set to different temperatures, e.g. 40 C, 60 C, 80 C, the required increase in heating current may be proportional to the difference of the material flow 20 temperature and the set temperature. Having three probes 5, it is possible to calculate a linear relation between the required resistive heater currents. During a resistive dip time, there are several features in the measured data that allow almost perfect water detection, such as:

The measured dips have different lengths, since time to dry depends on the set temperature.

The lowest heated probe will exhibit the longest dip and the hottest probe will exhibit the shortest dip. Any other dips e.g. caused by inhomogeneity of the material flow will not have this statistical connection and can therefore be excluded.

Under the presence of a resistive dip, the heater currents of all three heaters may rise and deviate substantially from the previous linear relationship. These indirect heat capacitance measurements enable more or less no β-error and self-calibrating on short time delays. Other advantages are that the temperature of the heated probe may e.g. be set to values below 100 C, that no evaporation is required and that the chill effect is sufficient.

According to some embodiments an alarm may be activated when the water is detected. The drilling may then be stopped automatically or manually by an operator.

According to some optional embodiments, since the paste, e.g. water-polluted dust, may accumulate on the sensor 4, power resistors, e.g. resistive heaters, may be arranged in thermal contact with the probes 5, allowing heating of the probes 5, e.g. above 100 C. Heating may evaporate the water traces and accelerate the return of the probes 5 into operational state.

According to some optional embodiments, since the paste, water-polluted dust may accumulate on the sensor 4, ultrasonic shakers may be arranged in mechanical contact with the probes 5 allowing more efficient dust removal. Ultrasonic shakers, when used herein, are intended to prevent the accumulation of material and the solidification of material so that the probes 5 are obscured from the material flow 20.

In an embodiment the arrangement 1, comprising programmable voltage waveform source and a programmable voltage waveform receiver, e.g. controllable AC voltage source amplifiers, and the control unit 2 including analog switches to allow comparison between reference impedances and measurement impedances and analog-digital converters. These are configured to provide data on the complex impedance between pairs of probes 5. At a given time, exactly one pair of probes 5 is active. The complex impedance data is read by the control unit 2 to calculate the necessary mean values and standard deviations. The control unit 2 is configured to save data for logging and improvement purposes. The control unit 2 provides a communication channel on which the state of the system may be transferred to the remote unit 6. The remote unit 6 has a receiver for said communication and provides means to indicate the status of the setup. The data may be transmitted in any known manner, such as e.g. by wire or wirelessly.

The embodiments herein provide a rapid reaction of detecting water in the material flow 20. The reaction may be in the order of milliseconds. Another advantage of embodiments herein is that the system performance can be programmed. Other advantages of embodiments herein are that the electronics used is simple and is built of common commercially available, multi sourced parts.

Figure 3:
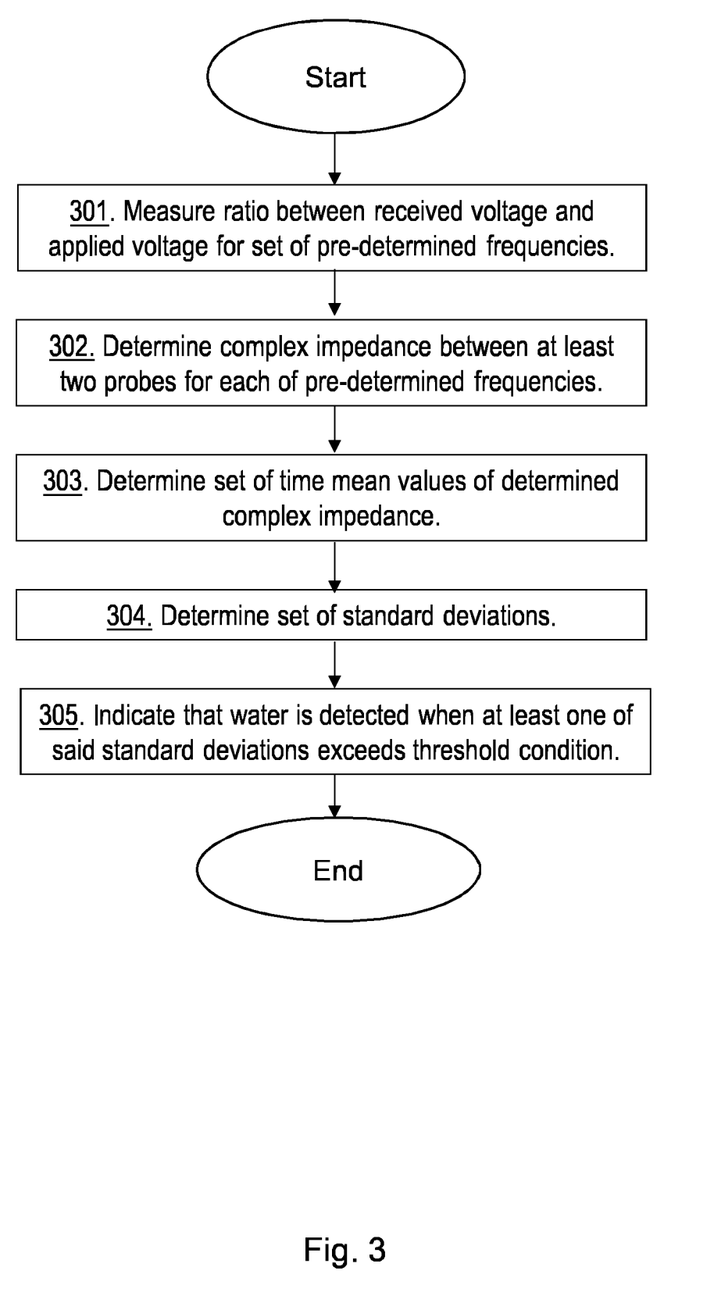
FIG. 3 is a flow chart showing a method for detecting water in a material flow during drilling.

An example method of how the embodiments herein may be employed in terms of actions is illustrated by the flow chart in FIG. 3. FIG. 3 thus illustrates an example method for detecting water in the material flow 20 during drilling. Some optional example embodiments that could be used in this procedure will also be described. The arrangement 1 comprises the control unit 2, the data acquisition unit 3, the sensor 4 and the drill rig 10. The sensor 4 comprises at least two probes 5, wherein the at least two probes 5 are to be arranged in contact with the material flow 20 and are connected to a programmable, e.g. tuneable, voltage source and a coherent programmable, e.g. tuneable, voltage receiver, which are capable of measuring the complex resistance between the probes 5.

Action 301 comprises measuring a ratio between a received voltage and an applied voltage, for a set of pre-determined frequencies. This ratio will be used to calculate the complex impedance. Said pre-determined frequencies may be associated to wavelengths much larger than the distance between the probes 5. This is advantageous because radiative effects, interferences are completely avoided. According to some embodiments, the pre-determined frequencies may be within the interval of 0.1 kHz-30 kHz. This interval may be chosen because of legal aspects. The detection system is in these cases is not considered as a generator of electromagnetic radiation. In addition, there are commercially available chipsets for impedance measurement in said frequency region.

Action 302 The impedance thus measured using a programmable sinusoid voltage source and a coherent detection, e.g. using applied voltage and received voltage. Using coherent detection, it is possible to calculate the real part of the complex impedance and the imaginary part of the complex impedance of the sensor 4 comprising the probes 5. The real part of the complex impedance is the conductivity and the imaginary part of the complex impedance the inductivity and capacitance. By tuning the measurement frequency within a predetermined interval it is possible to generate a spectrum of the complex impedance over frequency. Said spectrum is used to detect the presence of water traces. Thus, it is determined a complex impedance between the at least two probes 5 for each of the pre-determined frequencies, based on the measured ratio between the received voltage and the applied voltage.

Action 303 comprises determining a set of time mean values of the determined complex impedance, using a time window. Thus, without calculating any further material parameters, such as dielectric functions etc., a suitable time mean value of the determined complex impedance is determined, e.g. calculated, using a time window. With a suitable time mean value it is meant to establish mean values on the scale of some seconds at which the material flow 20 can be assumed to be constant. For example, measuring around 20 kHz-30 kHz, 10000 measurement points per second can be accomplished. Using e.g. 16 frequency steps, about 1000 measured impedance sets per second can be attained. Typically, 500-1000 measurement sets are integrated to produce a stable mean value. The presence of water comes in bursts and the transition between the last dry and wet state occurs within milliseconds, generating a deviation over 10-15 samples. Therefore, any mean value spanning integration over more than 10-15 samples may be acceptable. Integrating over too long times may cause the system to be sensitive to material changes in the material flow 20. This occurs on a second level. Translated to samples, it is generally unwise to integrate over more than 10000 samples. This mean value is calculated and updated all the time.

The measurement parameter is an instantaneous deviation of the mean value of the last few measured sets of impedances from the time mean value which is obtained by the mean value over a longer span of previously measured sets of impedances. Considering the calculation of a mean value as a low pass filtering process with a pre-determined integration time, the difference between two low pass filters may be used as measurement parameter. Said filters have different integration times. The integration time of the shorter, faster filter is determined by the noise of the measurement system, usually integration over 2-5 samples. The integration time of the longer, slower filter is determined by two requirements: It should be longer than the time at which typical impedance changes caused by water are reported, typically 10-15 samples, and it should be shorter than the time at which typical material flow parameters changes, typically 1000-10000 samples.

Action 304 comprises determining a set of standard deviations, based on the determined time mean value and the same time window. The standard deviation is determined and updated all the time. The deviation information is used to adapt the threshold condition at which the mean values from the previous action 303 are considered to be significant. In a typical setting, any instantaneous change exceeding 1.5-3 standard deviations are considered to be significant for water detection.

Action 305 comprises indicating that water is detected when at least one of said standard deviations exceeds a threshold condition. Strong deviations towards smaller absolute values in impedance indicate the presence of water traces. This effect is caused by the conductivity of water in the material flow 20. Generally, all water met in these conditions is salt contaminated. There is a pre-determined factor, typically 1.5-3.0, which is used to determine the threshold condition for the measurement parameter in relation to the above obtained standard deviations. As soon as the measurement parameter exceeds more than this threshold towards smaller impedances it is indicated that water is detected. An alarm may be activated when the water is detected and the drilling may then be stopped automatically or manually by the operator.

By following the above described method, the water detection during drilling is indicated in an enhanced and more efficient way. For the sake of clarity it should be understood that the steps may be repeated a number of times. Since the method is performed continuously during drilling this is usually the case.

According to some embodiments, each of the at least two probes 5 may comprise one or more heaters. The heaters may be resistive and there may be one heater per pair of probes 5. The heaters may be adapted to be controlled externally, e.g. in an on-off way, in order to stabilize the temperature to predetermined values.

According to some embodiments, one of the at least two probes 5 may comprise one or more heaters, wherein the heaters may be adapted to be controlled externally in order to stabilize the temperature to a set of predetermined values.

According to some embodiments, each of the at least two probes 5 may comprise one or more heaters, wherein the heaters are adapted to be controlled externally in order to monitor heating current and/or temperature. I.e. the ability to monitor the current through the heaters and/or the temperature of the heater has been added.

According to some embodiments, the sensor 4 comprises at least three probes 5, wherein each of the three probes 5 comprises one or more heaters. The heaters are adapted to be controlled externally in order to monitor heater current and in order to measure temperature.

The heaters described above may be resistive and there may be one heater per pair of probes 5.

It will be appreciated that the foregoing description and the accompanying drawings represent non-limiting examples of the method and arrangement taught herein. As such, the arrangement and techniques taught herein are not limited by the foregoing description and accompanying drawings. Instead, the embodiments herein are limited only by the following claims and their legal equivalents.

The invention claimed is:

1. An arrangement for detecting water in a material flow of particles during drilling, wherein the arrangement comprises a control unit, a data acquisition unit and a sensor, wherein the sensor comprises at least two probes, wherein the at least two probes are to be arranged in contact with the material flow of particles and are connected to a programmable voltage source and a programmable voltage receiver, and wherein the arrangement is configured to:
   measure a ratio between a received voltage waveform and an applied voltage waveform for a set of pre-determined frequencies;
   determine a complex impedance between the at least two probes for each of the pre-determined frequencies, based on the measured ratio;
   determine a set of time mean values of the determined complex impedance for each of the pre-determined frequencies, using a time window;
   determine a set of standard deviations, based on the determined time mean values; and
   indicate that water is detected when at least one of said standard deviations exceeds a threshold condition.

2. The arrangement according to claim 1, wherein each of the at least two probes comprises one or more heaters, wherein the heaters are adapted to be controlled externally in order to stabilize the temperature to predetermined values.

3. The arrangement according to claim 1, wherein one of the at least two probes comprises one or more heaters, wherein the heaters are adapted to be controlled externally in order to stabilize the temperature to predetermined values.

4. The arrangement according to claim 1, wherein each of the at least two probes comprises one or more heaters, wherein the heater current and/or heater temperature are adapted to be controlled externally in order to monitor current and/or temperature.

5. The arrangement according to claim 1, wherein the sensor comprises three probes, and wherein each of the three probes comprises one or more heaters, wherein the resistive heater current and/or heater temperature are adapted to be controlled externally in order to monitor current and/or temperature.

6. The arrangement according to claim 1, wherein the pre-determined frequencies are within the interval of 0.1-30 kHz.

7. The arrangement according to claim 1, wherein the probes are made of metal.

8. A drill rig comprising the arrangement according to claim 1.

9. A method for detecting water in a material flow of particles during drilling, the method comprising:
   measuring a ratio between a received voltage waveform and an applied voltage waveform for a set of pre-determined frequencies;
   determining a complex impedance between at least two probes for each of the pre-determined frequencies, based on the measured ratio;
   determining a set of time mean values of the determined complex impedance, using a time window;
   determining a set of standard deviations, based on the determined time mean value; and
   indicating that water is detected when at least one of said standard deviations exceeds a threshold condition.

10. The method according to claim 9, wherein each of the at least two probes comprises one or more heaters, wherein the heaters are controlled externally in order to stabilize the temperature to predetermined values.

11. The method according to claim 9, wherein one of the at least two probes comprises one or more heaters, wherein the heaters are controlled externally in order to stabilize the temperature to predetermined values.

12. The method according to claim 9, wherein each of the at least two probes comprises one or more heaters, wherein the heater current and/or heater temperature are controlled externally in order to monitor current and/or temperature.

13. The method according to claim 9, wherein the sensor comprises three probes, and wherein each of the three probes comprises one or more heaters, wherein the heater current and/or heater temperature are controlled externally in order to monitor current and/or temperature.

14. The method according to claim 9, wherein the predetermined frequencies are within the interval of 0.1 kHz-30 kHz.

15. The method according to claim 9, wherein the probes are made of metal.

16. The method according to claim 9 is performed in a drill rig.

\* \* \* \* \*